(12) United States Patent
Low et al.

(10) Patent No.: US 10,374,169 B2
(45) Date of Patent: Aug. 6, 2019

(54) ORGANIC HOLE TRANSPORT MATERIAL

(71) Applicant: GUANGDONG AGLAIA OPTOELECTRONIC MATERIALS CO. LTD, Foshan, Guangdong (CN)

(72) Inventors: Kam-Hung Low, Foshan (CN); Chin-Hsin Chen, Foshan (CN); Zhe Li, Foshan (CN); Lei Dai, Beijing (CN); Lifei Cai, Beijing (CN)

(73) Assignee: GUANGDONG AGLAIA OPTOELECTRONIC MATERIALS CO. LTD, Foshan (CN)

(*) Notice: Subject to any disclaimer, the term of this patent is extended or adjusted under 35 U.S.C. 154(b) by 0 days.

(21) Appl. No.: 16/060,936

(22) PCT Filed: Nov. 30, 2016

(86) PCT No.: PCT/CN2016/107852
§ 371 (c)(1),
(2) Date: Jun. 9, 2018

(87) PCT Pub. No.: WO2017/097152
PCT Pub. Date: Jun. 15, 2017

(65) Prior Publication Data
US 2018/0366655 A1    Dec. 20, 2018

(30) Foreign Application Priority Data
Dec. 9, 2015 (CN) .......................... 2015 1 0903881

(51) Int. Cl.
C07D 209/86 (2006.01)
H01L 51/00 (2006.01)
H01L 51/50 (2006.01)

(52) U.S. Cl.
CPC ........ *H01L 51/0072* (2013.01); *C07D 209/86* (2013.01); *H01L 51/0056* (2013.01); *H01L 51/0058* (2013.01); *H01L 51/5056* (2013.01); *H01L 51/5088* (2013.01)

(58) Field of Classification Search
USPC ........................................................ 548/440
See application file for complete search history.

(56) References Cited

U.S. PATENT DOCUMENTS

| 2014/0001446 A1 | 1/2014 | Mizuki et al. |
| 2017/0244047 A1 | 8/2017 | Lee et al. |

FOREIGN PATENT DOCUMENTS

| CN | 103959503 A | 7/2014 |
| KR | 101493482 B1 | 2/2015 |
| KR | 20150102733 A | 9/2015 |
| KR | 20150102735 A | 9/2015 |
| WO | 2015041428 A1 | 3/2015 |

OTHER PUBLICATIONS

Liu, Y. et al. J. Mater. Chem. C, 2, 8736-8744 (2014) (Year: 2014).*
Joswick and Campbell, "Systematic investigation of the effects of organic film structure on light emitting diode performance" Journal of Applied Physics 80, 2883 (Sep. 1996); doi: 10.1063/1.363140.

* cited by examiner

*Primary Examiner* — Nyeemah A Grazier
(74) *Attorney, Agent, or Firm* — Maschoff Brennan

(57) ABSTRACT

The present invention relates to an organic hole transport material having a compound of the structure shown in formula (I), wherein R1-R2 independently represent hydrogen, C1-C8 substituted or substituted alkyl, C2-C8 substituted or unsubstituted alkenyl, C2-C8 substituted or unsubstituted alkynyl, or C6-C10 substituted or substituted aryl, the substituents being C1-C4 alkyl or halogen. Device experiments show that the organic hole transport material of the present invention has high glass-transition temperature and high thermal stability; a hole-only organic semiconductor diode device and an organic electroluminescent device manufactured by the organic hole transport material have good hole transport performance, high and stable current efficiency, and a long device life.

7 Claims, 7 Drawing Sheets

ORGANIC HOLE TRANSPORT MATERIAL

TECHNICAL FIELD

The present invention relates to a novel organic hole transport material, which is formed into a thin film by vacuum deposition and used as an electron transport material for a hole-only organic semiconductor diode device.

BACKGROUND ART

A hole-only organic semiconductor diode device is one type of single-carrier devices and is used as a power semiconductor device for a switch or a rectifier of a smart digital power integrated circuit. The hole transport material of the present invention can also be applied to organic electroluminescent devices and field effect transistors.

The hole-only organic semiconductor diode device is a device that is manufactured by spin-coating or depositing one or more layers of organic materials between two electrodes made of metal, inorganic compounds or organic compounds. A classical single-layer hole-only organic semiconductor diode device includes an anode, a hole transport layer, and a cathode. A hole injection layer may be added between an anode and a hole transport layer of a multi-layer hole-only organic semiconductor diode device, and an electron barrier layer may be added between the hole transport layer and a cathode. The electron barrier layer, the hole transport layer and the hole injection layer are composed of an electron barrier material, a hole transport material and a hole injecting material, respectively. After a voltage connected to the hole-only organic semiconductor diode device reaches a turn-on voltage, holes generated by the anode are transported through the hole transport layer to the cathode, and conversely, electrons cannot be injected from the cathode. The hole transport material in the hole-only organic semiconductor diode device can be applied to other semiconductor devices such as an organic electroluminescent device. The organic electroluminescent device has a huge market, so the stable and efficient organic hole transport material plays an important role in the application and promotion of organic electroluminescent devices, and is also an urgent need for the application and promotion of organic electroluminescent large-area panel display.

An existing hole transport material tris(4-carbazol-9-yl-phenyl) amine (TCTA) which is frequently used in the market can basically meet the market demand of organic electroluminescent panels, but its efficiency and stability still need to be further improved because of its low glass-transition temperature (151° C.). The TCTA material has the disadvantage of easy crystallization. Once the hole transport material crystallizes, a charge transfer mechanism among molecules is different from an amorphous film mechanism that operates normally, resulting in a change in the hole transport properties. When the hole transport material is used in the organic electroluminescent device, the electrical conductivity of the entire device will change after a period of time, causing electron and hole charge mobility to become unbalanced, resulting in decrease of performance of the device and local short-circuiting possibly occurring in the device, and thereby affecting the stability of the device, and even resulting in failure of the device (Reference document: Journal of Applied Physics 80, 2883 (1996); doi: 10.1063/1.363140). Therefore, the demand for research and development of a novel hole transport material with a high glass-transition temperature is very urgent.

SUMMARY OF THE INVENTION

In view of the defects of the above materials, the present invention provides an organic hole transport material that has high morphological stability and may be applied to a long-life hole-only organic semiconductor diode device and an organic electroluminescent device, and has good hole transport performance and high current efficiency.

An organic hole transport material has a compound of a structure shown in formula (I),

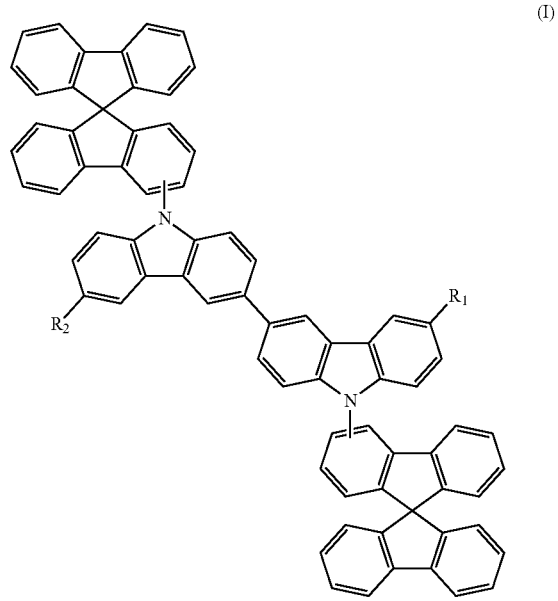

(I)

wherein R1-R2 independently represent hydrogen, C1-C8 substituted or substituted alkyl, C2-C8 substituted or unsubstituted alkenyl, C2-C8 substituted or unsubstituted alkynyl, or C6-C10 substituted or substituted aryl, the substituents being C1-C4 alkyl or halogen.

Preferably, R1-R2 independently represent hydrogen, C1-C4 substituted or substituted alkyl, C2-C4 substituted or unsubstituted alkenyl, C2-C4 substituted or unsubstituted alkynyl, or substituted or substituted aryl.

Preferably, R1-R2 independently represent hydrogen, C1-C4 substituted or substituted alkyl, phenyl, naphthyl, C1-C4 alkyl substituted phenyl or naphthyl.

Preferably, R1 is identical with R2.

Preferably, R1-R2 preferably represent hydrogen.

The compound shown in formula (I) is the following compound having the structures:

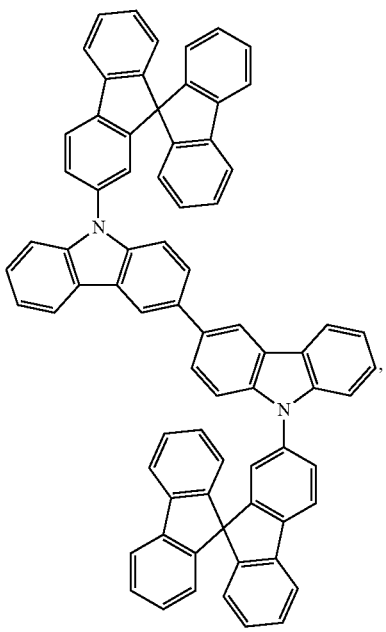

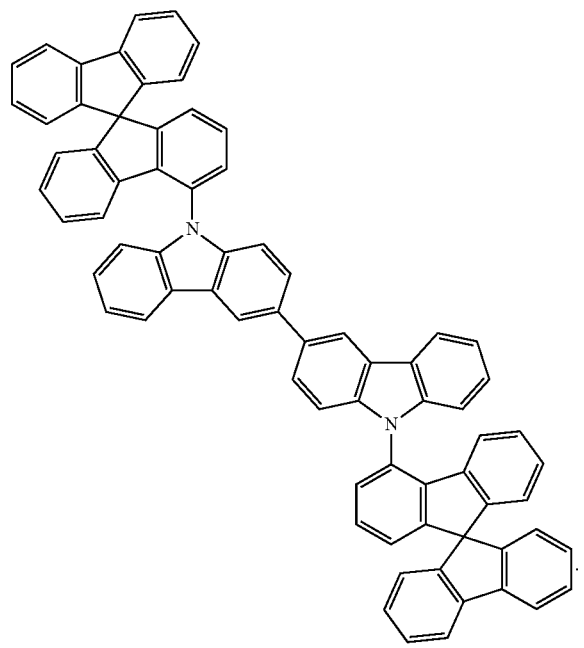

The organic layer is one or more of an electron barrier layer, a hole transport layer, and a hole injection layer. It should be pointed out in particular that these organic layers mentioned above can be present as required, rather than every layer being present.

The electron barrier layer, the hole transport layer and/or the hole injection layer contain the compound of the formula (I).

The compound of formula (I) is a hole transport material.

The total thickness of the organic layers of the electronic device of the present invention is 1 nm to 1000 nm, preferably 1 nm to 500 nm, and more preferably 5 nm to 300 nm.

The organic layer may be formed into a thin film by evaporation or a solution method.

As mentioned above, the compounds of formula (I) of the present invention are as follows, but are not limited to the structures listed:

1

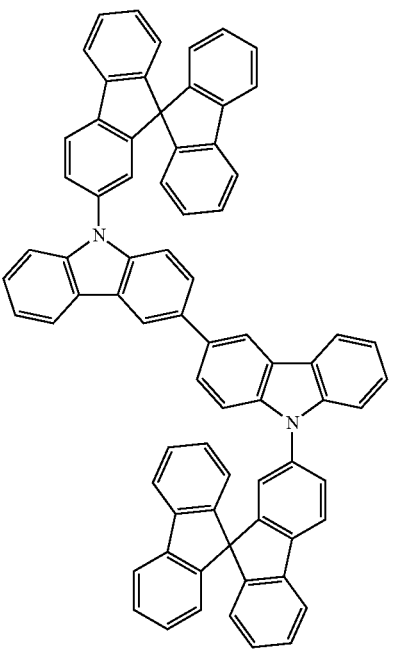

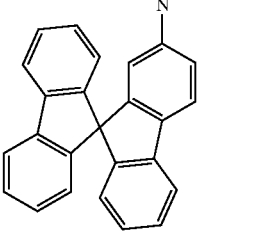

2

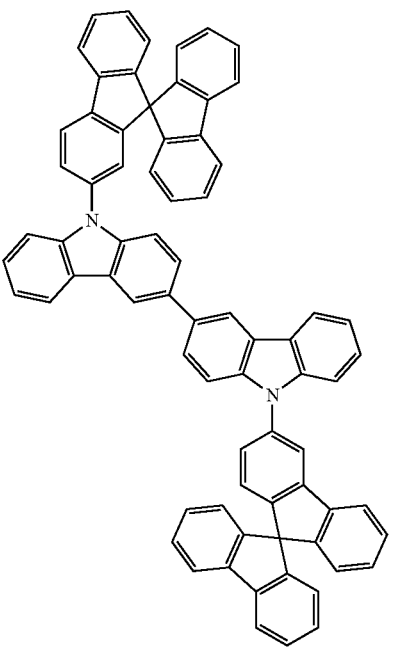

3
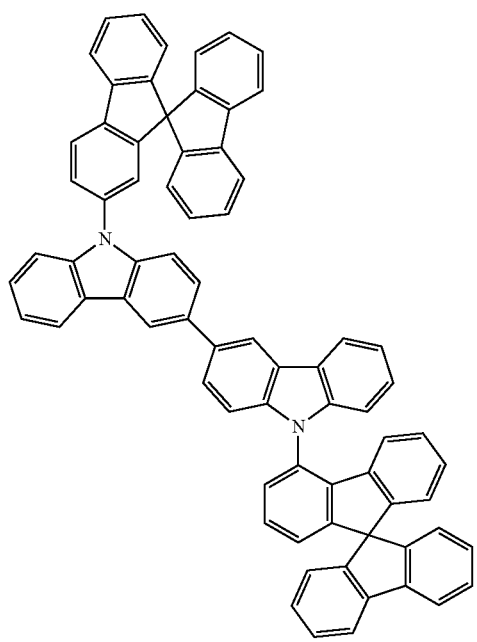
4
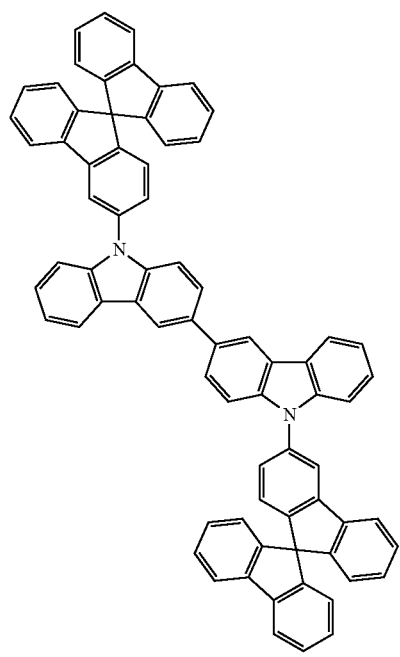
5
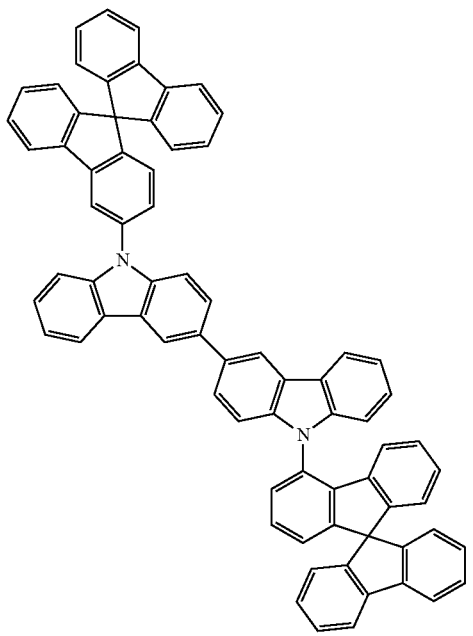
6

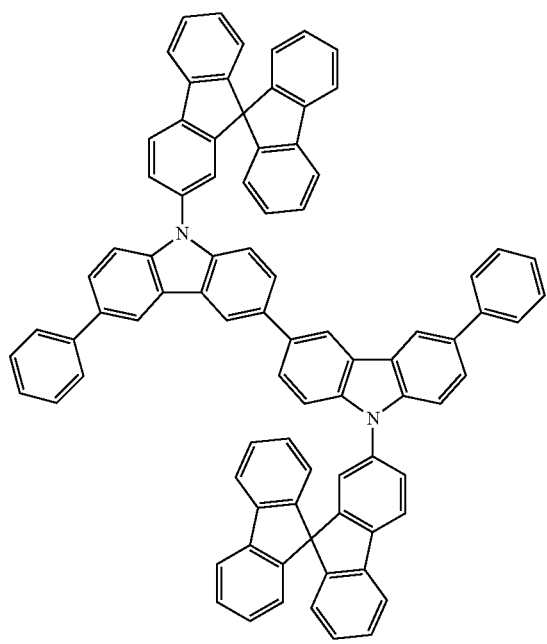

7

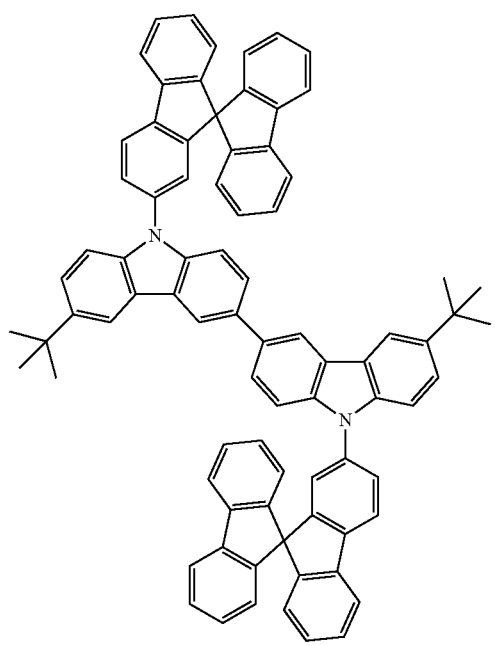

8

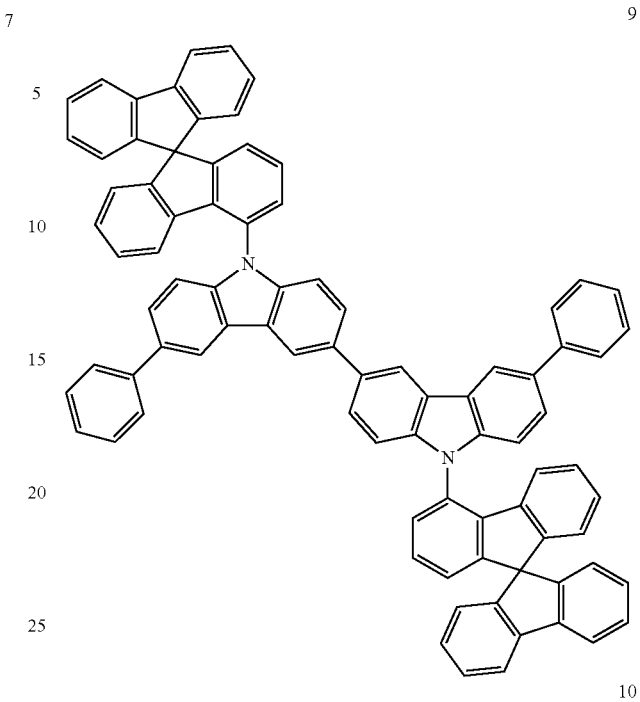

9

10

Device experiments show that the organic hole transport material of the present invention has high glass-transition temperature and high thermal stability. The hole-only organic semiconductor diode device and the organic electroluminescent device manufactured by the organic hole transport material have good hole transport performance, high and stable current efficiency, and a long device life.

DETAILED DESCRIPTIONS OF THE PREFERRED EMBODIMENTS

Figure 1:
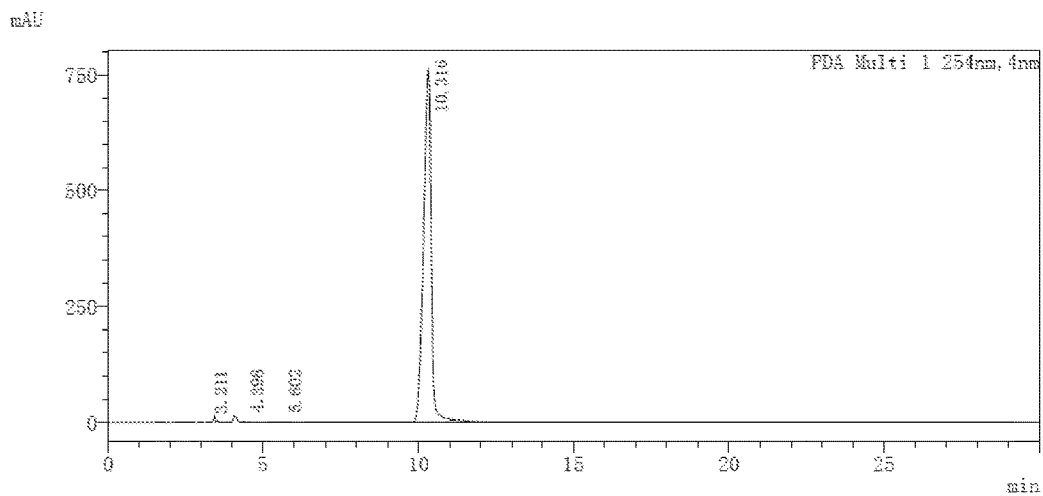
FIG. 1 is an HPLC diagram of a compound 1.

In order to describe the present invention in more detail, the following examples are given, but the present invention is not limited to these.

Example 1

Synthesis Route of Compound 1

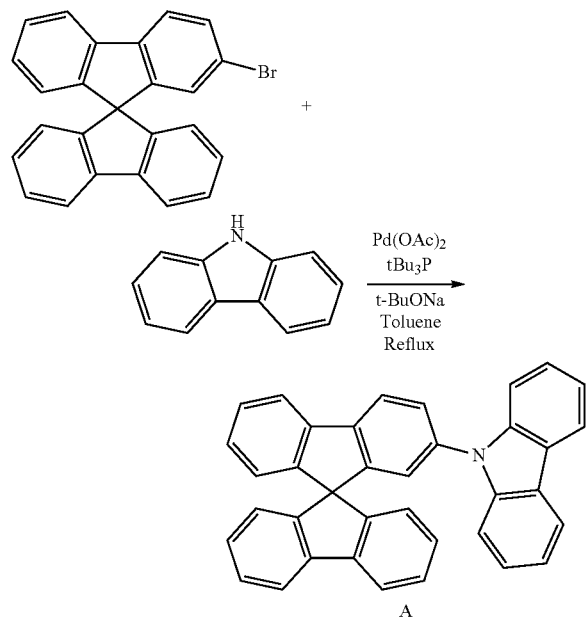

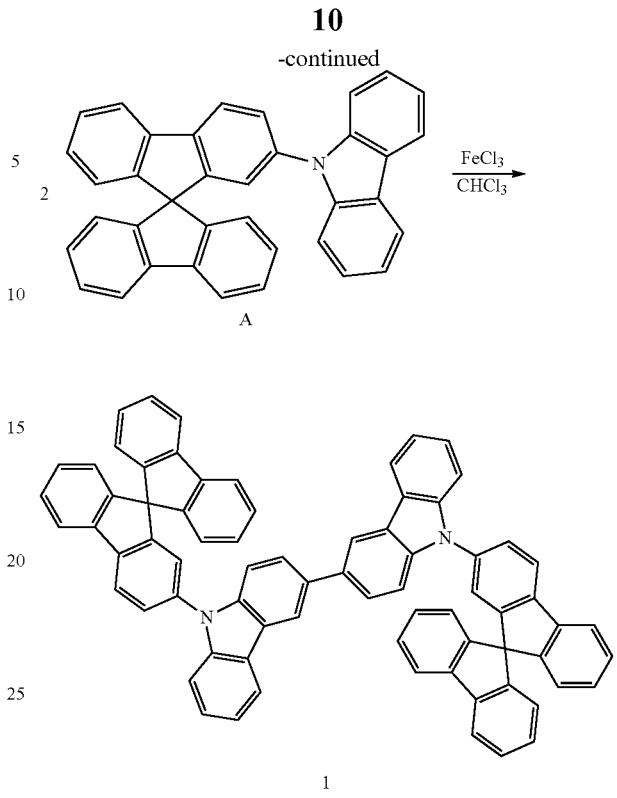

Synthesis of Compound A

Reaction delivery: sequentially adding 2-bromo-9,9-spirobifluorene (5.00 g, 13 mmol), carbazole (1.77 g, 11 mmol), palladium acetate (120 mg), and sodium tert-butoxide (1.30 g) to a three-neck flask; after sucking air and pumping nitrogen three times, adding previously taken anhydrous toluene (80 mL) into the flask in the presence of nitrogen; finally, injecting tri-tert-butylphosphine (8 mL, 50% toluene solution) into a reaction solution via a syringe, wherein the reaction temperature is 110° C. and the reaction time is 15 h.

Post-treatment: spin-drying the reaction solution, dissolving in $CH_2Cl_2$, and extracting with an equal volume of water for three times; spin-drying an organic layer, and adding a small amount of $CH_2Cl_2$ again until solid is just dissolved; adding methanol for recrystallization, and then separating colorless transparent crystals out from the solution.

Treatment after reaction: stopping heating to cool to 20° C.; adding methanol (100 mL) and stirring for 2 h to separate solid out; washing a filter cake with methanol and drying in vacuum to obtain a crude product; adding the crude product with ethyl acetate, and pulping to obtain a yellow compound A (4.10 g, yield 77.5%, HPLC purity 99.0%). $^1$H NMR (300 MHz, CDCl3, δ) 8.10-8.01 (m, 3H), 7.93 (d, J=7.5 Hz, 1H), 7.81 (d, J=7.5 Hz, 2H), 7.58 (dd, J=8.0, 1.9 Hz, 1H), 7.48-7.26 (m, 5H), 7.25-7.12 (m, 7H), 6.96-6.78 (m, 4H). $^{13}$C NMR (76 MHz, CDCl3) δ 151.03, 149.25, 148.30, 141.93, 141.14, 141.03, 140.78, 137.16, 128.33, 128.13, 128.11, 126.59, 125.99, 124.44, 124.10, 123.44, 122.89, 121.26, 120.39, 120.37, 120.00, 109.88, 66.32.

Synthesis of Compound I

Reaction delivery: sequentially adding a compound A (8.01 g, 16.6 mmol), anhydrous ferric chloride (7.98 g, 49 mmol), and chloroform (160 mL) to a 250-mL round-bottom flask; after introducing and pumping nitrogen three times, performing a reflux reaction at 70° C. for 24 h in the presence of nitrogen.

Post-treatment: performing spotting with dichloromethane and petroleum ether according to a ratio of 1:4, wherein the product point emits intense blue light at a 365-nm wavelength UV lamp, and the Rf value is 0.3 or so; spin-drying the reaction solution directly, dissolving in dichloromethane, and extracting three times with an equal volume of water; performing recrystallization is performed three times using chloroform and methanol to obtain a white solid (2.7 g, yield 68%), with a purity of 99.9% after sublimation (the conditions of the liquid phase are as follows: chromatographic column: Inertsil ODS-SP 4.6*250 mm, 5 μm, column temperature: 40° C., solvent: THF, mobile phase: MeOH-THF (90:10) (v/v), detection wavelength: 254 nm), see FIG. 1. The peak statistics are shown in the table below.

| | "Peak Table" PDA CH1 254 nm | | | | | |
|---|---|---|---|---|---|---|
| Peak No. | Retention Time | Area | Height | Concentration | Area % | Height |
| 1 | 3.211 | 647 | 114 | 0.000 | 0.005 | 0.015 |
| 2 | 4.398 | 6768 | 853 | 0.000 | 0.052 | 0.112 |
| 3 | 5.602 | 2944 | 302 | 0.000 | 0.022 | 0.040 |
| 4 | 10.316 | 13078449 | 759835 | 0.000 | 99.921 | 99.833 |
| Total | | 13088808 | 761104 | | 100.000 | 100.000 |

Figure 2:
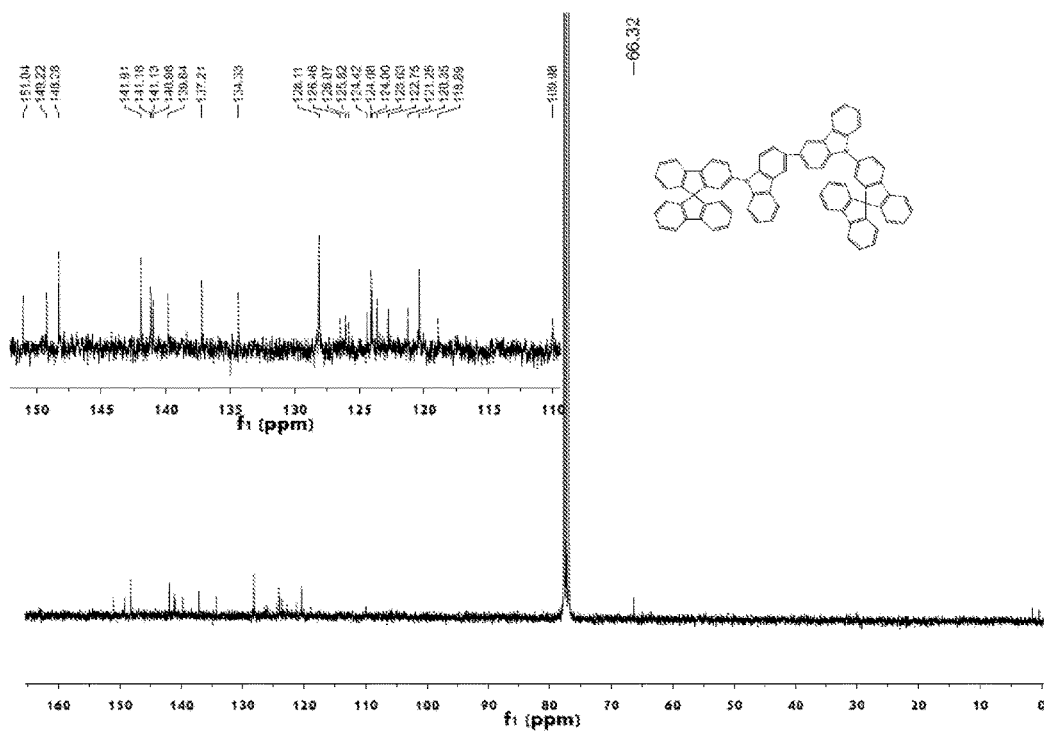
FIG. 2 is a carbon spectrogram of the compound 1.

$^{13}$C NMR (76 MHz, CDCl$_3$) δ: 151.04, 151.04, 149.22, 148.28, 141.91, 141.18, 141.13, 140.98, 139.84, 137.21, 134.33, 128.11, 124.42, 124.08, 124.00, 123.63, 122.75, 121.25, 120.35, 118.89, 109.95, 66.32, see FIG. 2.

Figure 3:
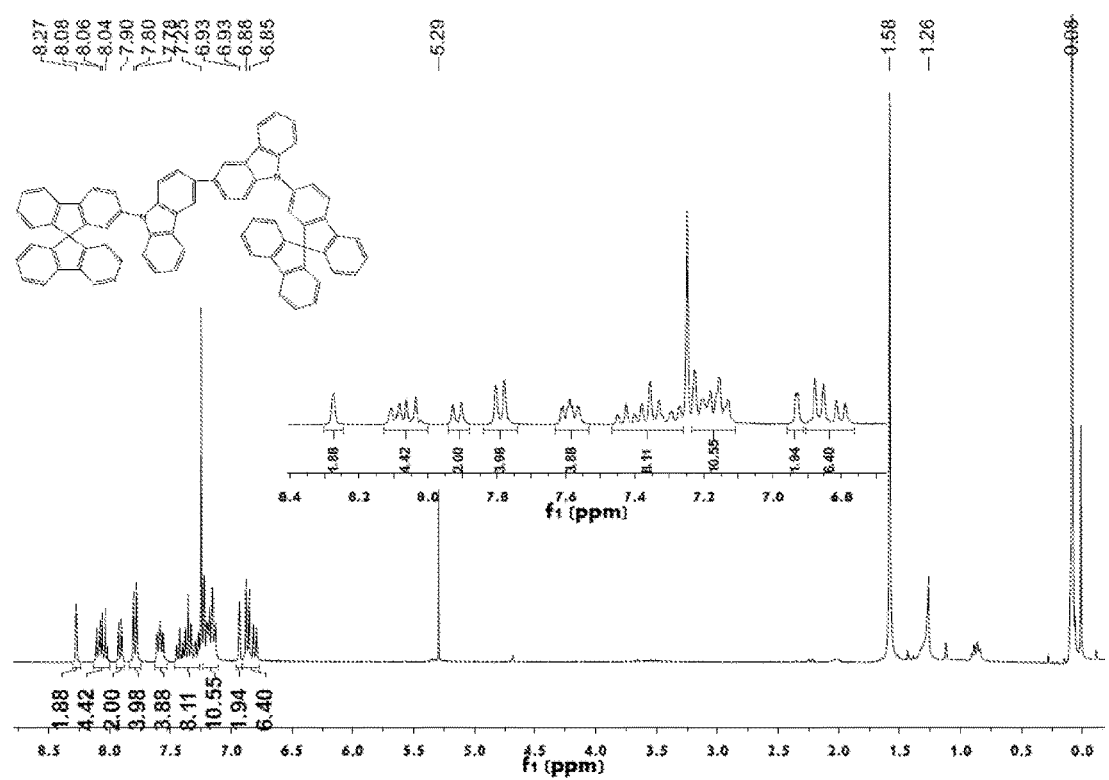
FIG. 3 is a hydrogen spectrogram of the compound 1.

$^1$H NMR (300 MHz, CDCl$_3$, δ) 8.27 (s, 2H), 8.12-8.03 (m, 4H), 7.91 (d, J=7.5 Hz, 2H), 7.77 (d, J=7.5 Hz, 4H), 7.61-7.56 (m, 4H), 7.45-7.26 (m, 10H), 7.24-7.11 (m, 10H), 6.94-6.77 (m, 8H), see FIG. 3.

Figure 4:
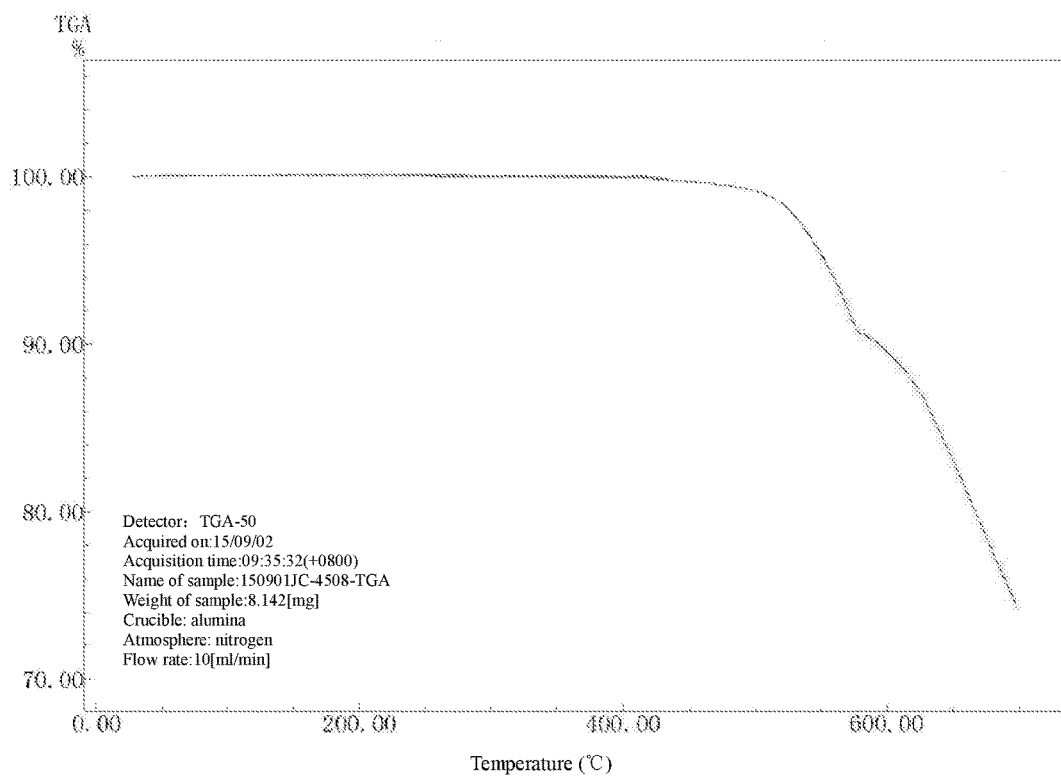
FIG. 4 is a thermal analysis—TGA diagram of the compound.

The TGA diagram is shown in FIG. 4.

The glass-transition temperature is 218° C.

Example 2

Preparation of Hole-Only Organic Semiconductor Diode Device 1

The hole-only organic semiconductor diode device is manufactured by an organic hole transport material of the present invention.

First, a transparent conductive ITO glass substrate 10 (with an anode 20 on the top) is sequentially washed with a detergent solution and deionized water, ethanol, acetone and deionized water, and then subject to oxygen plasma treatment for 30 seconds.

Then, HATCH which is 5 nm thick is evaporated on ITO as a hole injection layer 30.

Then, a compound 1 which is 100 nm thick is evaporated on the hole injection layer as a hole transport layer 40.

Then, TAPC which is 5 nm thick is evaporated on the hole transport layer as an electron barrier layer 50.

At last, aluminum which is 100 nm thick is evaporated on the electron barrier layer as a device cathode 60.

Figure 5:
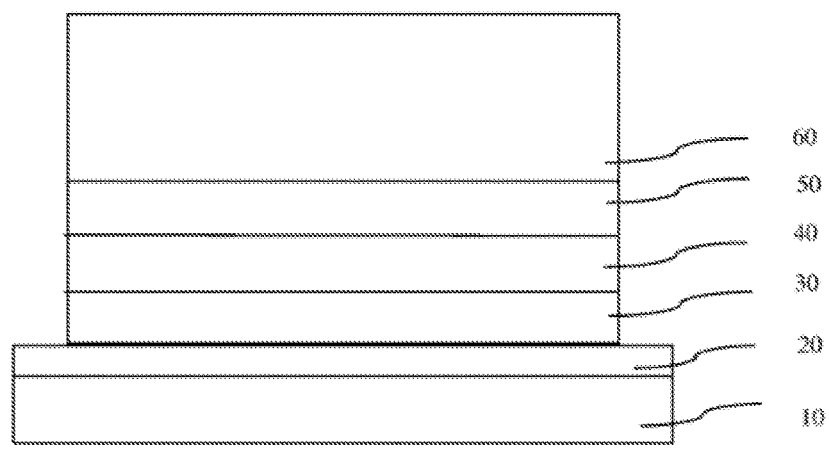
FIG. 5 is a structural diagram of a hole-only organic semiconductor diode device according to the present invention, wherein 10 represents a glass substrate, 20 represents an anode, 30 a hole barrier layer, 40 an electron transport layer, 50 an electron injection layer, and 60 a cathode.

The structure is as shown in FIG. 5.

The structural formulas in the device are as follows:

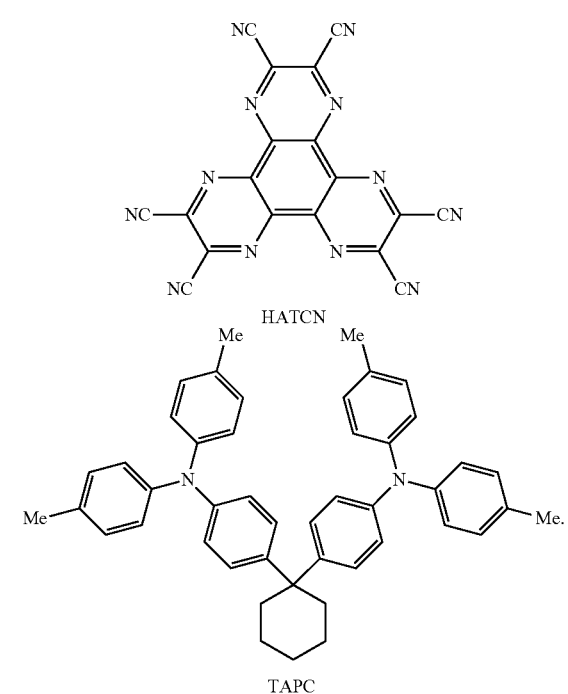

HATCN

TAPC

By using the space charge limited current (SCLC), the relationship between the current density and the electric field intensity is as shown in equation (1):

$$J = \frac{9}{8}\varepsilon\varepsilon_0 \frac{E^2}{L} \mu_0 \exp(\beta\sqrt{E}) \quad (1)$$

wherein, J is a current density (mA cm$^{-2}$), ε is a relative dielectric constant (it is generally 3 in an organic material), ε$_0$ is a vacuum dielectric constant (8.85×10$^{-14}$ C V$^{-1}$ cm$^{-1}$), E is an electric field intensity (V cm$^{-1}$), L is a thickness (cm) of a sample in the device, μ$_0$ is an electric charge mobility (cm$^2$ V$^{-1}$ s$^{-1}$) under zero electric field, and β is a Poole-Frenkel factor which indicates how fast the mobility changes with the electric field intensity.

Comparative Example 1

Preparation of Hole-Only Organic Semiconductor Diode Device 2

The method is the same as that of example 2, but the common commercially available compound TCTA is used as the hole transport layer 40 to manufacture a comparative hole-only organic semiconductor diode device.

The structural formula in the device is as follows:

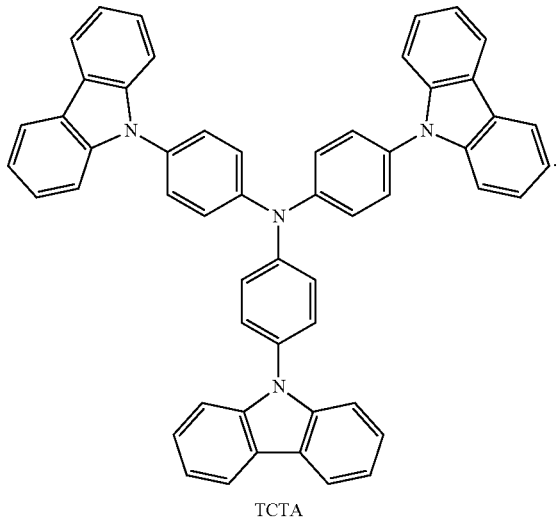 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

TCTA

Figure 6:
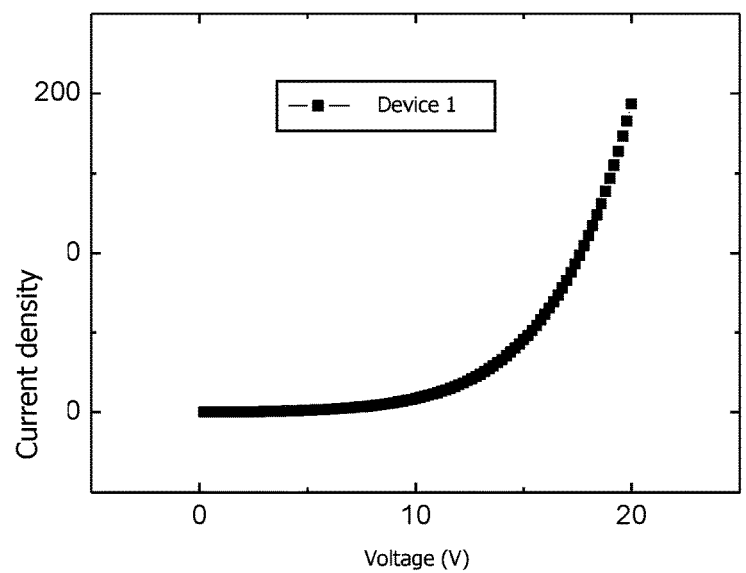
FIG. 6 is a voltage-current density diagram of a device 1 of the present invention.
Figure 7:
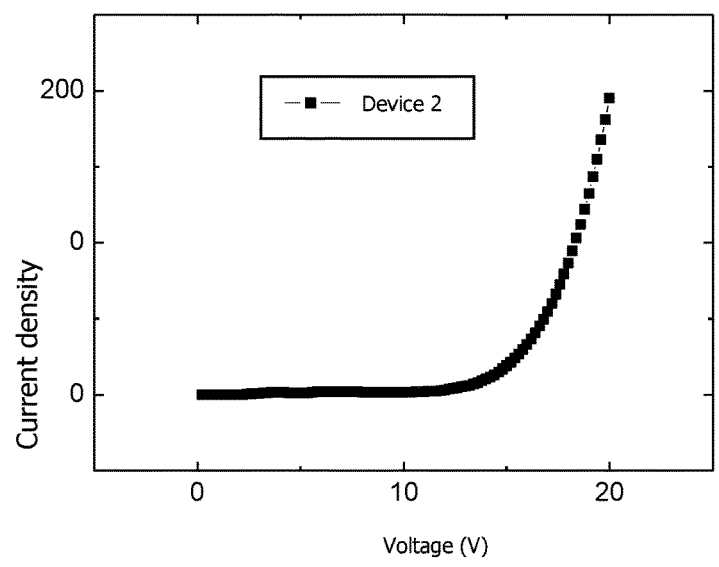
FIG. 7 is a voltage-current density diagram of a comparative device 2 of the present invention.

The voltage-current density is as shown in FIG. 6 and FIG. 7.

Hole Mobility of the Manufactured Device ($cm^2 V^{-1} s^{-1}$)

| Device No. | μ0 | Electron Mobility $1 \times 10^6$ V/cm under an operating electric field |
|---|---|---|
| 1 | $4.46 \times 10^{-6}$ | $3.94 \times 10^{-4}$ |
| 2 | $1.99 \times 10^{-10}$ | $4.93 \times 10^{-5}$ |

The electron mobility of the device 1 and the electron mobility of the device 2 under an operating electric field of $1 \times 10^6$ V/cm are calculated according to formula (1) and data in FIGS. 6 and 7. As can be seen from the results, the electron mobility $3.94 \times 10^{-4}$ of the device 1 under the operating electric field of $1 \times 10^6$ V/cm is higher than the electron mobility $4.93 \times 10^{-5}$ of the device 2, which indicates that an organic-only semiconductor diode device 1 manufactured by the organic hole transport material compound 1 of the present invention has better hole transport properties than the commercially available compound TCTA.

Example 2

Figure 8:
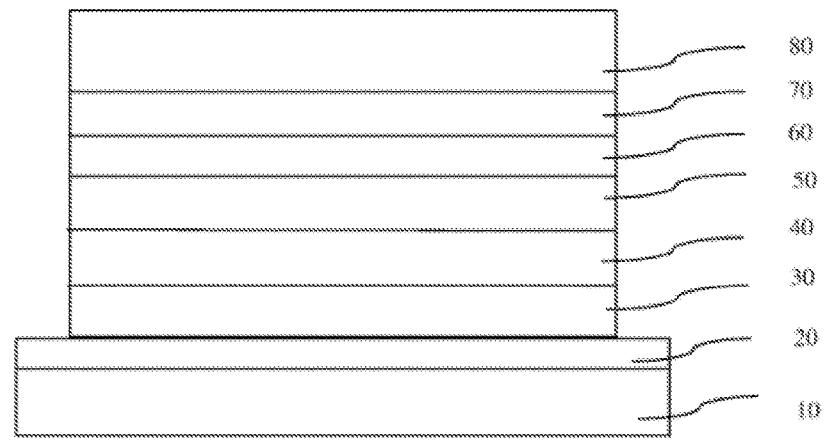
FIG. 8 is a structural diagram of an organic electroluminescent device according to the present invention, wherein 10 represents a glass substrate, 20 represents an anode, 30 a hole injection layer, 40 a hole transport layer, 50 a light emitting layer, 60 an electron transport layer, 70 an electron injection layer, and 80 a cathode.
Figure 9:
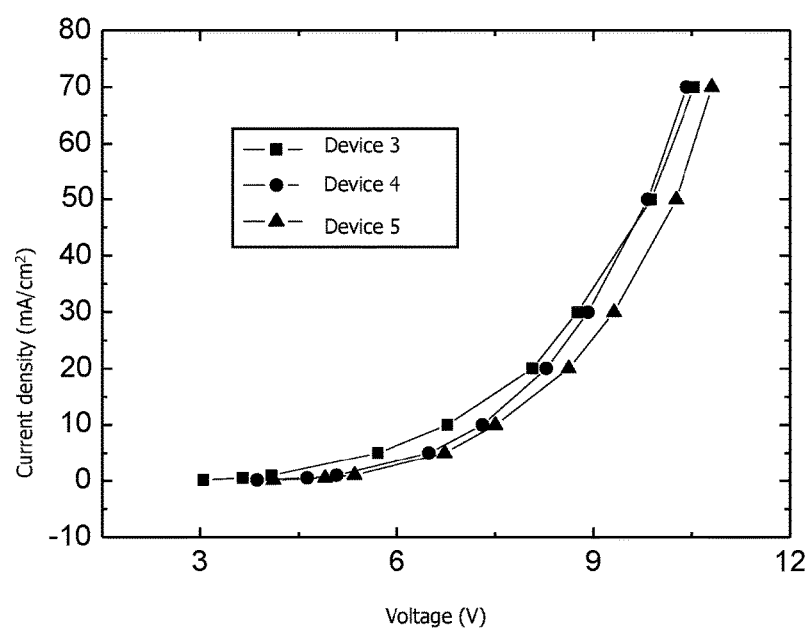
FIG. 9 is a voltage-current density diagram of devices 3, 4 and 5 of the present invention.
Figure 10:
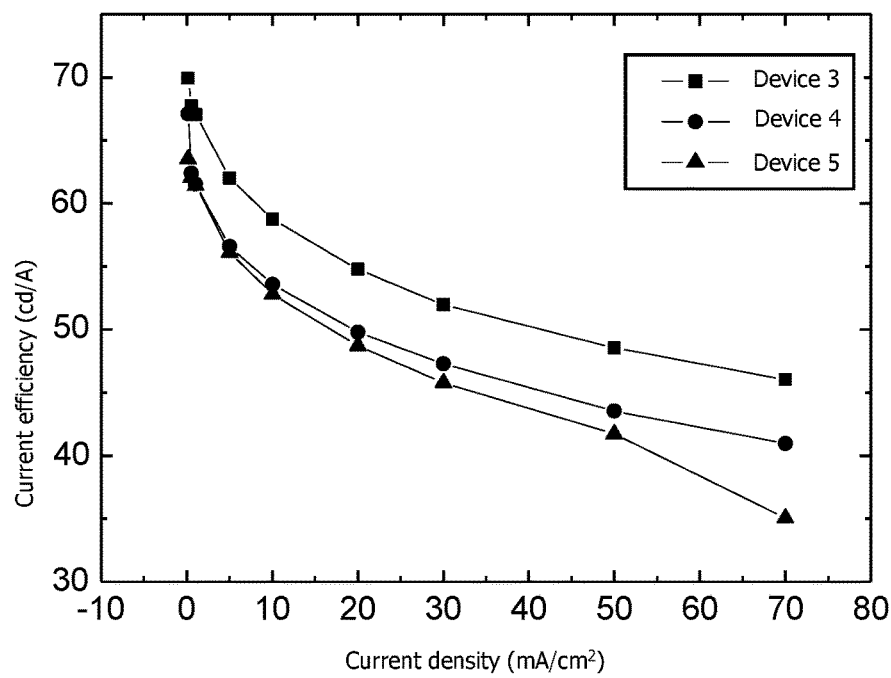
FIG. 10 is a voltage-current effect diagram of the devices 3, 4 and 5 of the present invention.

Preparation of Organic Electroluminescent Device 3
OLED is manufactured by the organic electronic material of the present invention.
First, a transparent conductive ITO glass substrate 10 (with an anode 20 on the top) is sequentially washed with a detergent solution and deionized water, ethanol, acetone and deionized water, and then subject to oxygen plasma treatment for 30 seconds.
Then, HATCH which is 90 nm thick is evaporated on ITO as a hole injection layer 30.
Then, a compound 1 is evaporated to form a hole transport layer 40 which is 30 nm thick.
Then, a compound B (2%) which is 40 nm thick and a compound C (98%) are evaporated on the hole transport layer as a light emitting layer 50.
Then, BPhen which is 40 nm thick is evaporated on the light emitting layer as an electron transport layer 60.
At last, LiQ which is 15 nm thick is evaporated as an electron injection layer 70 and Al which is 150 nm thick is evaporated as a device cathode 80.
The structure is as shown in FIG. 8.

Example 3

Preparation of Organic Electroluminescent Device 4
OLED is manufactured by the organic electronic material of the present invention.
First, a transparent conductive ITO glass substrate 10 (with an anode 20 on the top) is sequentially washed with a detergent solution and deionized water, ethanol, acetone and deionized water, and then subject to oxygen plasma treatment for 30 seconds.
Then, the compound 1 which is 90 nm thick is evaporated on ITO as a hole injection layer 30.
Then, a compound D is evaporated to form a hole transport layer 40 which is 30 nm thick.
Then, a compound B (2%) which is 40 nm thick and a compound C (98%) are evaporated on the hole transport layer as a light emitting layer 50.
Then, BPhen which is 40 nm thick is evaporated on the light emitting layer as an electron transport layer 60.
At last, LiQ which is 15 nm thick is evaporated as an electron injection layer 70 and Al which is 150 nm thick is evaporated as a device cathode 80.

Example 4

Preparation of Organic Electroluminescent Device 5
OLED is manufactured by a commercially available organic electronic material.
First, a transparent conductive ITO glass substrate 10 (with an anode 20 on the top) is sequentially washed with a detergent solution and deionized water, ethanol, acetone and deionized water, and then subject to oxygen plasma treatment for 30 seconds.
Then, HATCH which is 90 nm thick is evaporated on ITO as a hole injection layer 30.
Then, a compound D is evaporated to form a hole transport layer 40 which is 30 nm thick.
Then, a compound B (2%) which is 40 nm thick and a compound C (98%) are evaporated on the hole transport layer as a light emitting layer 50.
Then, BPhen which is 40 nm thick is evaporated on the light emitting layer as an electron transport layer 60.
At last, LiQ which is 15 nm thick is evaporated as an electron injection layer 70 and Al which is 150 nm is evaporated as a device cathode 80.
The performance data of the device is as shown in FIGS. 9-13.
As can be seen from FIGS. 9-10 and from the comparison of the device 3 and the device 5, the hole transport performance of the compound 1 is superior to that of the comparative compound D; as can be seen from the comparison of the device 4 and the device 5, the compound 1 also has excellent hole injection performances and can be one of excellent candidates of a hole injection material.

Figure 11:
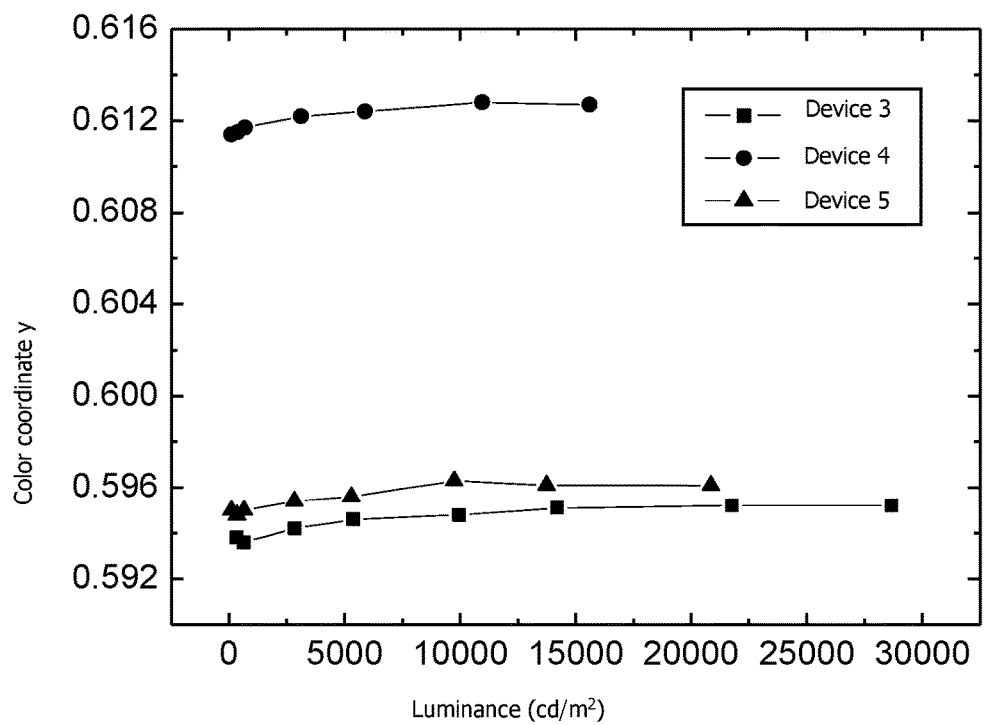
FIG. 11 is a luminance-color coordinate y diagram of the devices 3, 4, and 5 of the present invention.
Figure 12:
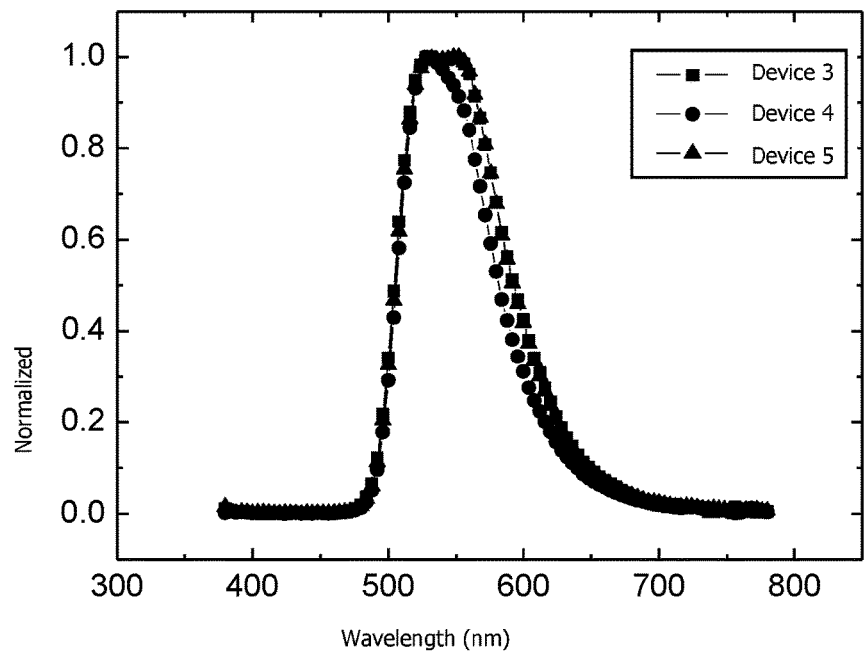
FIG. 12 is an emission spectrum diagram of the devices 3, 4, and 5 of the present invention.

The followings can be calculated from FIGS. 11-12:

The manufactured device 3, under an operating current density of 20 mA/cm², has a luminance of 9966 cd/m², a current efficiency up to 49.8 cd/A, EQE of 14.67 under 18.8 lm/W, as well as a CIEx of 0.369 and a CIEy of 0.595 of green light emission.

The manufactured device 4, under an operating current density of 20 mA/cm², has a luminance of 10961 cd/m², a current efficiency up to 54.7 cd/A, EQE of 15.80 under 21.3 lm/W, as well as a CIEx of 0.350 and a CIEy of 0.613 of green light emission.

The manufactured device 5, under an operating current density of 20 mA/cm², has a luminance of 9750 cd/m², a current efficiency up to 48.7 cd/A, EQE of 14.3 under 18.2 lm/W, as well as a CIEx of 0.369 and a CIEy of 0.596 of green light emission.

Figure 13:
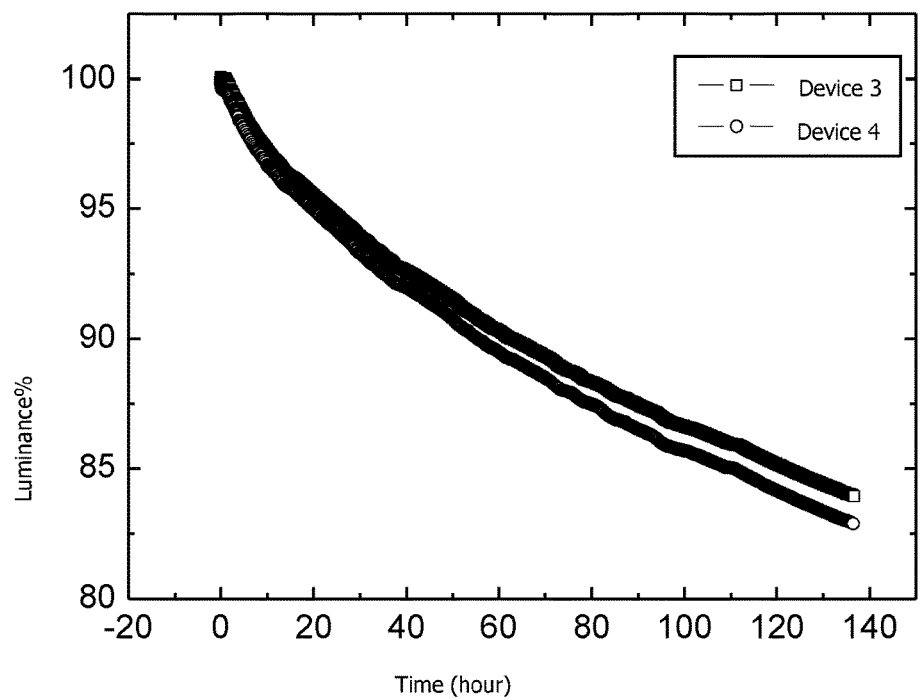
FIG. 13 is a time-luminance diagram of the devices 3 and 4 of the present invention.

As can be seen in FIG. 13, at a starting luminance of 7000 cd/m², the tested device 3 LT90=60 h and the device 4 LT90=51 h.

Compound B

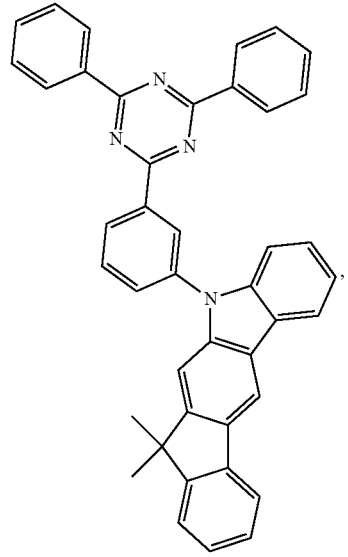

Compound C

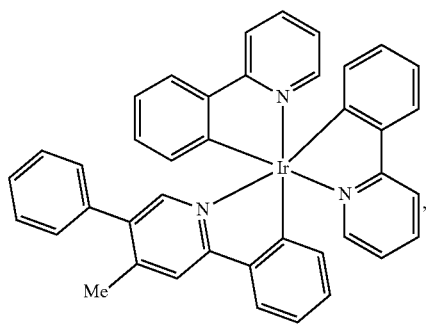

Compound D

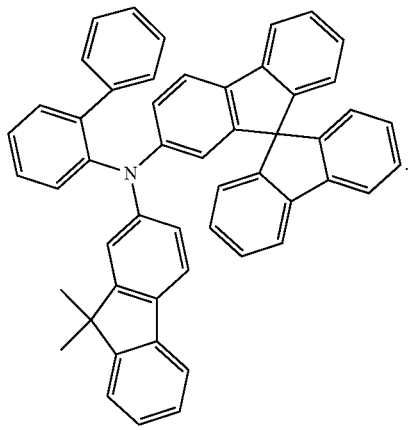

The invention claimed is:
1. An organic hole transport material having a compound of a structure shown in formula (I)

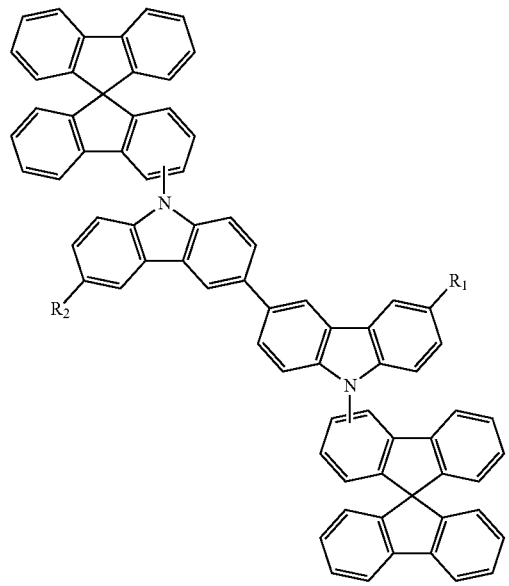

(I)

wherein R1-R2 independently represent hydrogen, C1-C8 substituted or substituted alkyl, C2-C8 substituted or unsubstituted alkenyl, C2-C8 substituted or unsubstituted alkynyl, or C6-C10 substituted or substituted aryl, the substituents being C1-C4 alkyl or halogen.

2. The organic hole transport material according to claim 1, wherein R1-R2 independently represent hydrogen, C1-C4 substituted or substituted alkyl, C2-C4 substituted or unsubstituted alkenyl, C2-C4 substituted or unsubstituted alkynyl, or substituted or substituted aryl.

3. The organic hole transport material according to claim 2, wherein R1-R2 independently represent hydrogen, C1-C4 substituted or substituted alkyl, phenyl, naphthyl, or C1-C4 alkyl substituted phenyl or naphthyl.

4. The organic hole transport material according to claim 3, wherein R1 is identical with R2.
5. The organic hole transport material according to claim 4, having a compound of a structure:
1
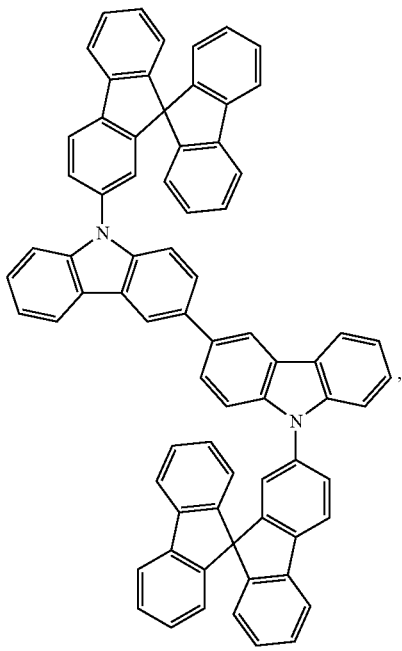
,
2
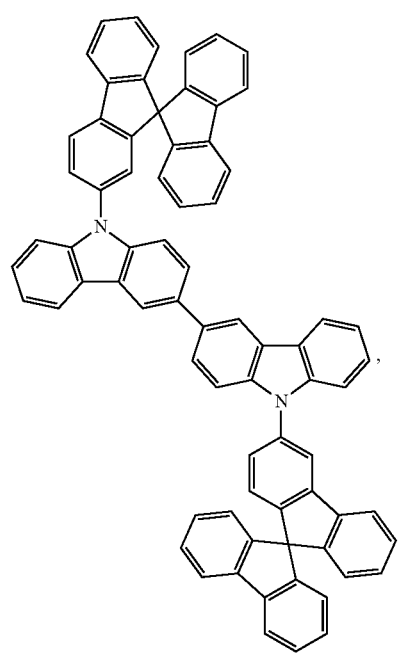
,
-continued
3
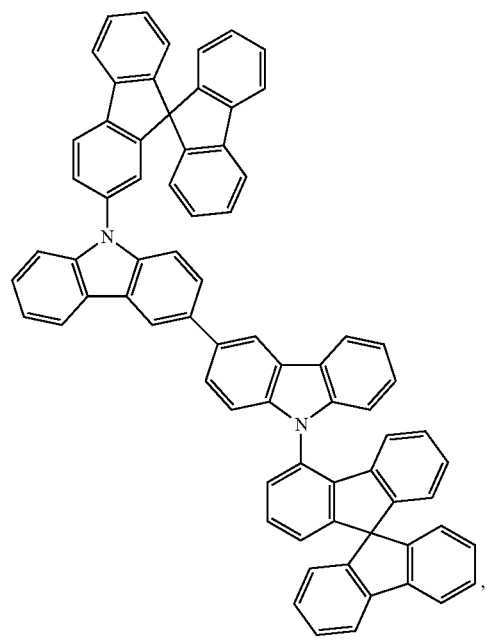
,
4
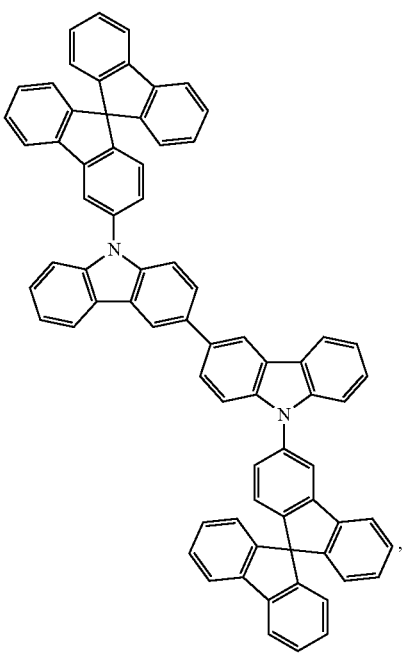
,

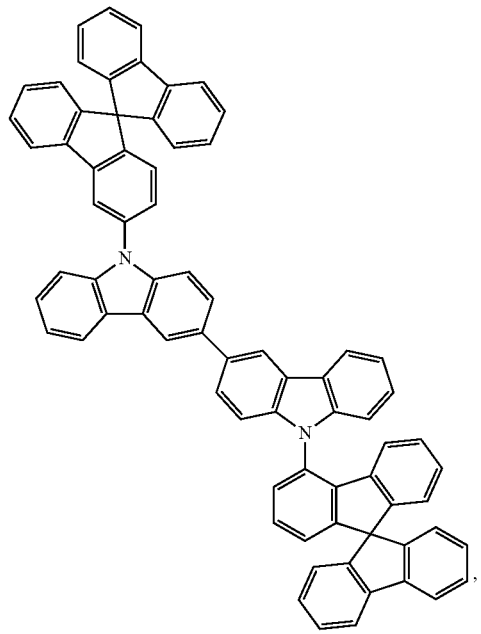
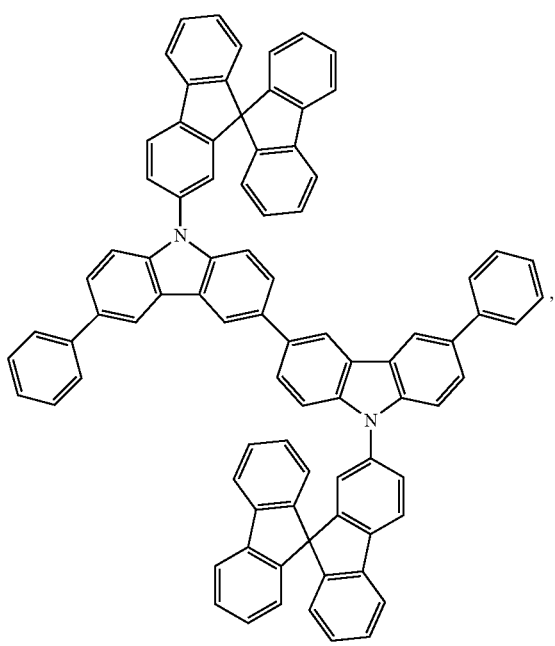
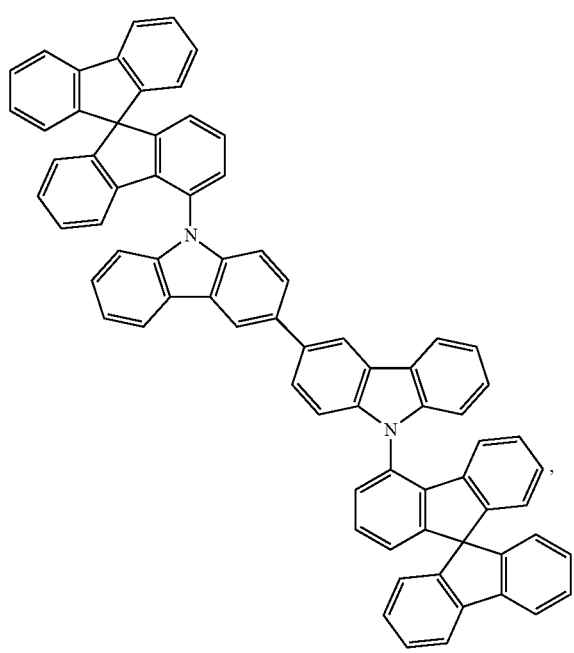
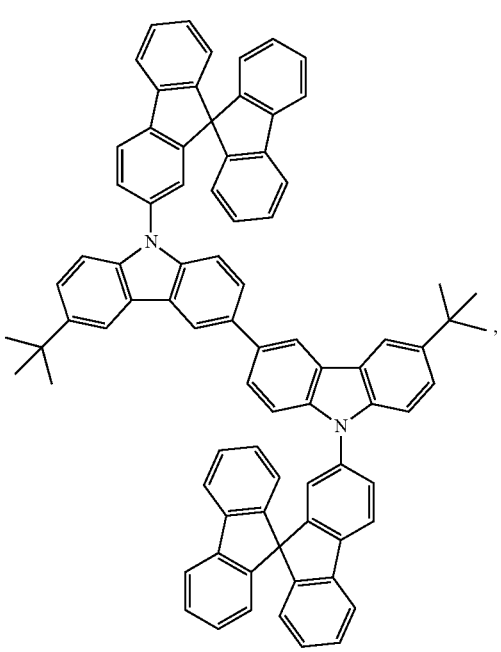

-continued
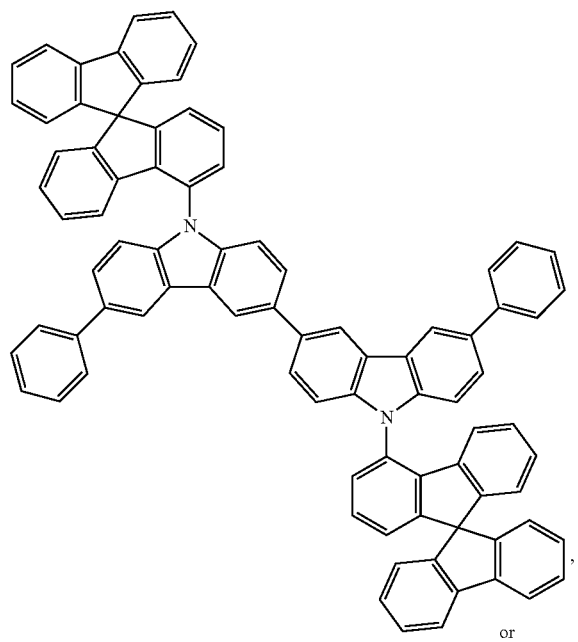
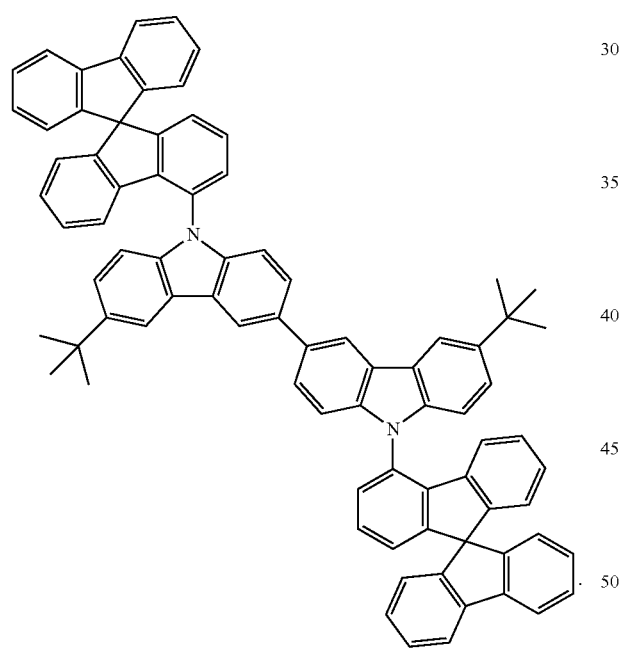
6. The organic hole transport material according to claim 4, wherein R1 and R2 are hydrogen.
7. The organic hole transport material according to claim 6, having a compound of a structure:
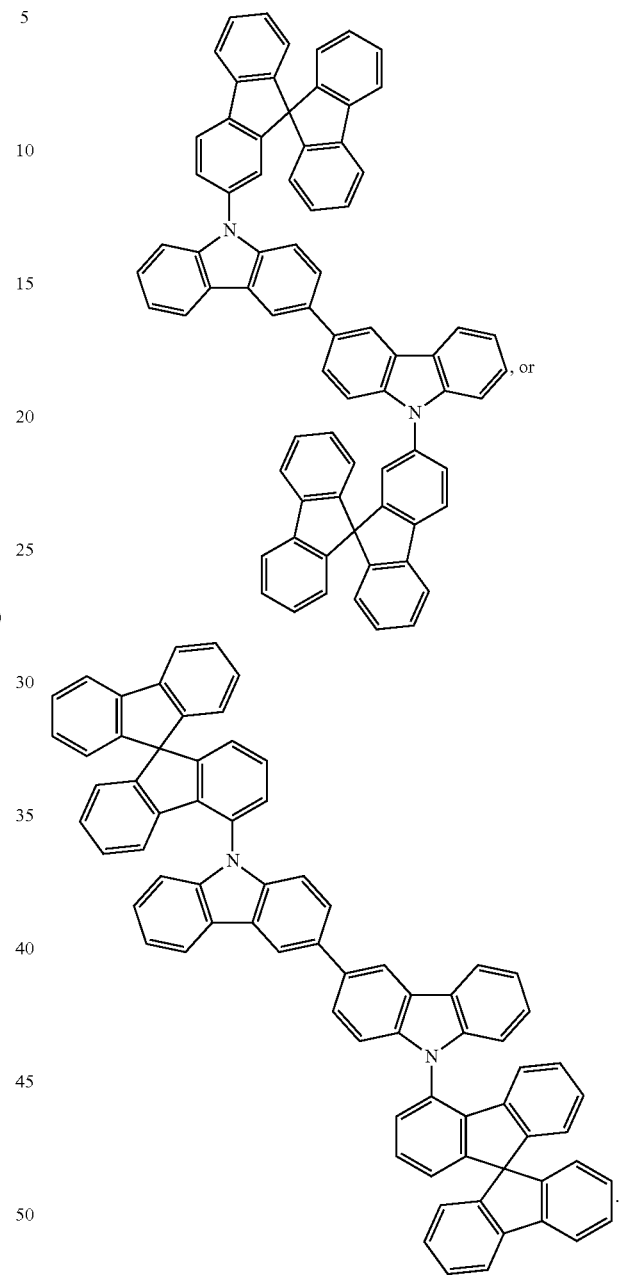
* * * * *